(12) United States Patent
Nagasaka

(10) Patent No.: US 11,170,501 B2
(45) Date of Patent: Nov. 9, 2021

(54) IMAGE ANALYSIS DEVICE

(71) Applicant: Toru Nagasaka, Nagoya (JP)

(72) Inventor: Toru Nagasaka, Nagoya (JP)

( * ) Notice: Subject to any disclaimer, the term of this patent is extended or adjusted under 35 U.S.C. 154(b) by 62 days.

(21) Appl. No.: 16/609,123

(22) PCT Filed: May 9, 2017

(86) PCT No.: PCT/JP2017/017559
§ 371 (c)(1),
(2) Date: Oct. 28, 2019

(87) PCT Pub. No.: WO2018/207261
PCT Pub. Date: Nov. 15, 2018

(65) Prior Publication Data
US 2020/0211182 A1    Jul. 2, 2020

(51) Int. Cl.
*G06T 7/00* (2017.01)
*G06T 7/62* (2017.01)
(Continued)

(52) U.S. Cl.
CPC .......... *G06T 7/0012* (2013.01); *G06K 9/6267* (2013.01); *G06N 20/00* (2019.01);
(Continued)

(58) Field of Classification Search
CPC ..... G06T 7/0012; G06T 7/62; G06T 7/70–74; G06T 2207/10056; G06T 2207/10024;
(Continued)

(56) References Cited

U.S. PATENT DOCUMENTS 5,313,532 A    5/1994 Harvey et al.
9,471,977 B2*  10/2016 Ozaki ................ G06K 9/00147
(Continued)

FOREIGN PATENT DOCUMENTS

JP    2003191189 A    7/2003
JP    2009236728 A    10/2009
(Continued)

OTHER PUBLICATIONS

Written Opinion of the International Searching Authority for PCT Application No. PCT/JP2017/017559 dated Aug. 22, 2017 (English translation).
(Continued)

*Primary Examiner* — Vu Le
*Assistant Examiner* — Julius Chai
(74) *Attorney, Agent, or Firm* — K&L Gates LLP

(57) ABSTRACT

An image analysis device may include a memory storing learning data for executing image analysis, and may obtain cell image data representing a cell image including a plurality of cell objects, sequentially identify plural pieces of partial image data from the cell image data, sequentially execute a center determination process on each of the plural pieces of partial image data, classify at least one cell corresponding to at least one cell object among a plurality of cell objects by using results of the center determination process on the plural pieces of partial image data and classification data included in learning data, and output a classification result.

16 Claims, 17 Drawing Sheets

(51) Int. Cl.
  *G06T 7/73* (2017.01)
  *G06N 20/00* (2019.01)
  *G06K 9/62* (2006.01)

(52) U.S. Cl.
  CPC .................. *G06T 7/62* (2017.01); *G06T 7/74* (2017.01); *G06T 2207/20081* (2013.01); *G06T 2207/30024* (2013.01)

(58) Field of Classification Search
  CPC ........... G06T 2207/20081; G06T 2207/30024; G06N 20/00; G06K 9/6267; G06K 9/00127; G06K 9/00147; G06K 9/0014
  See application file for complete search history.

(56) References Cited

U.S. PATENT DOCUMENTS

| | | | |
|---|---|---|---|
| 2006/0204953 A1* | 9/2006 | Ptitsyn | G06T 7/0012 435/4 |
| 2008/0166035 A1* | 7/2008 | Qian | G06T 7/0012 382/133 |
| 2010/0002920 A1 | 1/2010 | Cosatto et al. | |
| 2011/0019898 A1 | 1/2011 | Takagi et al. | |
| 2015/0138334 A1* | 5/2015 | Usuba | G06K 9/00127 348/79 |

FOREIGN PATENT DOCUMENTS

| | | |
|---|---|---|
| JP | 2011027542 A | 2/2011 |
| JP | 2011052700 A | 3/2011 |
| JP | 2011527055 A | 10/2011 |
| JP | 2013065156 A | 4/2013 |
| WO | 2018207261 A1 | 11/2018 |

OTHER PUBLICATIONS

Wang et al., Segmenting subcellular structures in histology tissue images, 2015 IEEE 12th International Symposium on Biomedical Imaging (ISBI), pp. 556-559.
Alegro et al., Automating cell detection and classification in human brain fluorescent in microscopy images using dictionary learning and sparse coding, Journal of Neuroscience Methods (Mar. 4, 2017), 282:20-33.
Lal Das et al., Random-forest-based automated cell detection in Knife-Edge Scanning Microscope rat Nissl data, 2015 International Joint Conference on Neural Networks (IJCNN), Killarney, 2015, pp. 1-8.
Extended European Search Report for European Application No. 17909404.0 dated Apr. 29, 2020.
International Search Report and Written Opinion for PCT/JP2017/017559 dated Aug. 22, 2017 (English translation).

* cited by examiner (Case A)

(Case A)

(Case A)

(Case A)

(Case B)

(Case B)

(Case B)

(Case B)

(Case C)

(Case C)

(Case C)

(Case C)

IMAGE ANALYSIS DEVICE

CROSS-REFERENCE TO RELATED APPLICATIONS

This application is a U.S. National Stage Entry under 35 U.S.C. §371 of International Patent Application No. PCT/JP2017/017559, filed May 9, 2017, entitled IMAGE ANALYSIS DEVICE, the entire disclosure of which is hereby incorporated by reference herein in its entirety and for all purposes.

TECHNICAL FIELD

The disclosure herein discloses art that classifies a cell corresponding to a cell object by analyzing an image including the cell object.

BACKGROUND ART

In recent years, histopathologic diagnosis or cytological diagnosis using an image analysis device has been practiced (for example, Japanese Patent Application Publication No. 2011-527055). In these techniques, data for classifying cells is learned by an image analysis device in advance and image data obtained from a histopathologic specimen or a cytological specimen is inputted to the image analysis device, to obtain a cell classification result.

SUMMARY OF INVENTION

Technical Problem Normally in pathological diagnosis assistance or automatic cell analysis using an image analysis device, plural pieces of partial image data are identified sequentially from inputted cell image data. Then, for each of the plural pieces of partial image data, a cell that corresponds to a cell object included in a partial image represented by the partial image data is classified. However, for example, when a cell is located at a position deviated from the center of a partial image, there is a possibility that the cell cannot accurately be classified by using such partial image. The disclosure herein discloses art for improving accuracy of cell classification.

An image analysis device disclosed herein may comprise: a memory that stores learning data for image analysis, the learning data including determination data and classification data, the determination data being for determining whether a center of an analysis target image matches a center of a cell object, the classification data being for classifying a cell corresponding to a cell object; an obtaining unit configured to obtain cell image data representing a cell image including a plurality of cell objects; a first image identifying unit configured to identify plural pieces of partial image data sequentially from the cell image data; a determining unit configured to execute a center determination process for each of the plural pieces of partial image data sequentially, the center determination process including determining, by using the determination data included in the learning data, whether a center of a partial image represented by process target partial image data matches a center of a cell object; a classifying unit configured to classify at least one cell corresponding to at least one cell object among the plurality of cell objects by using a result of the center determination process for each of the plural pieces of partial image data and the classification data included in the learning data; and an output unit configured to output a classification result.

According to the above configuration, the image analysis device executes the center determination process for each of the plural pieces of partial image data by using the determination data. By doing so, the image analysis device can suitably determine whether the center of each partial image matches the center of the corresponding cell object. Further, the image analysis device classifies at least one cell based on the result of the center determination process and the classification data. Due to this, accuracy of cell classification can be improved.

The image analysis device may further comprise a generating unit configured to generate binary image data by binarizing the cell image data. The first image identifying unit may identify the plural pieces of partial image data sequentially by repeating detection and identification, the detection being for detecting a position of a candidate object, which is a cell object candidate, from a binary image represented by the binary image data, the identification being for identifying partial image data corresponding to the detected position from the cell image data. The image analysis device may further comprise a second image identifying unit, wherein in a case where it is determined in the center determination process for first partial image data among the plural pieces of partial image data that a center of a first partial image represented by the first partial image data does not match a center of a cell object and the first partial image includes a target cell object, the second image identifying unit identifies second partial image data that represents a second partial image including the target cell object from the cell image data, wherein a center of the second partial image matches a center of the target cell object. The classifying unit may classify a cell corresponding to the target cell object by using the second partial image data and the classification data. According to this configuration, the image analysis device can classify a cell using the second partial image data. Since the center of the second partial image matches the center of the target cell object, the accuracy of the cell classification is improved.

The image analysis device may further comprise: a position identifying unit configured to identify a center position of the target cell object included in the first partial image in the case where it is determined in the center determination process for the first partial image data that the center of the first partial image does not match the center of the cell object and the first partial image includes the target cell object; and a changing unit configured to change the binary image data by writing a predetermined mark at a position corresponding to the center position in the binary image represented by the binary image data. The second image identifying unit may detect a position of the predetermined mark from a changed binary image represented by the changed binary image data so as to identify the second partial image data corresponding to the position of the predetermined mark from the cell image data. According to this configuration, the image analysis device can be suppressed from classifying the same cell multiple times.

In a case where it is determined that the center of the first partial image does not match the center of the cell object and the first partial image includes only one target cell object, the position identifying unit may identify one center position. The changing unit may change the binary image data by writing one predetermined mark at one position corresponding to the one center position in the binary image represented by the binary image data. The second image identifying unit may detect a position of the one predetermined mark from the changed binary image represented by the changed binary image data so as to identify the second partial image data corresponding to the position of the one predetermined mark from the cell image data. According to this configuration, the image analysis device can suitably identify one piece of the second partial image data when the first partial image includes only one target cell object.

In a case where it is determined that the center of the first partial image does not match the center of the cell object and the first partial image includes two or more target cell objects, the position identifying unit may identify two or more center positions. The changing unit may change the binary image data by writing two or more predetermined marks at two or more positions corresponding to the two or more center positions in the binary image represented by the binary image data. The second image identifying unit may detect each of positions of the two or more predetermined marks from the changed binary image represented by the changed binary image data so as to identify two or more second partial image data corresponding to the positions of the two or more predetermined marks from the cell image data. According to this configuration, the image analysis device can suitably identify two or more second partial image data when the first partial image includes two or more target cell objects.

In a case where the two or more target cell objects include a first cell object having a first center position that is a first distance apart from the center of the first partial image and a second cell object having a second center position that is a second distance apart from the center of the first partial image, the position identifying unit may identify the two or more center positions including the first center position and the second center position. The second distance may be longer than the first distance. The changing unit may change the binary image data by writing the two or more predetermined marks at the two or more positions corresponding to the two or more center positions including the first center position and the second center position in the binary image represented by the binary image data. According to this configuration, the image analysis device can suitably write the predetermined marks even when distances between the center of the first partial image and each of the center positions of the cell objects are not constant.

The first image identifying unit may identify sequentially the plural pieces of partial image data that represent a plurality of partial images obtained by scanning the cell image with a predetermined interval. According to this configuration, the image analysis device can identify the respective pieces of partial image data while suppressing processing load.

In a case where it is determined in the center determination process for process target partial image data among the plural pieces of partial image data that a center of a partial image represented by the process target partial image data matches a center of a cell object, the classifying unit may classify a cell corresponding to the cell object. In a case where it is determined in the center determination process for process target partial image data among the plural pieces of partial image data that a center of a partial image represented by the process target partial image data does not match a center of a cell object, the classifying unit may not execute the classification using the partial image. According to this configuration, the image analysis device does not execute the classification when determining that the center of the partial image does not match the center of the cell object in the center determination process. Thus, when the cell object is located at a position deviated from the center of the partial image, the image analysis device does not classify the cell corresponding to this cell object. Due to this, erroneous classification of cells can be suppressed.

The image analysis device may further comprise: a generating unit configured to generate binary image data by binarizing the cell image data; a position identifying unit, wherein in a case where it is determined in the center determination process for process target partial image data among the plural pieces of partial image data that a center of a partial image represented by the process target partial image data does not match a center of a cell object and the partial image includes a target cell object, the position identifying unit identifies a center position of the target cell object; and a changing unit configured to change the binary image data by writing a predetermined mark at a position corresponding to the center position in the binary image represented by the binary image data. The classifying unit may: detect a position of the predetermined mark from a changed binary image represented by the changed binary image data; identify partial image data corresponding to the detected position from the cell image data; and classify a cell corresponding to the target cell object included in a partial image represented by the partial image data by using the partial image data and the classification data. According to this configuration, the image analysis device can classify the cell by using the partial image data corresponding to the position of the predetermined mark. Here, since the predetermined mark is written at the position corresponding to the center position of the target cell object, the center of the partial image represented by that partial image data can match the center of the target object cell. Due to this, the accuracy of the cell classification is improved.

The learning data may be data for executing image analysis according to a convolutional neural network or image analysis according to a large-scale network including a convolutional neural network as a partial structure thereof. According to this configuration, the image analysis device can execute image analysis using the convolutional neural network according to the learning data, that is, the image analysis that uses deep learning and artificial intelligence. Especially, the larger a volume of the learning data is, the more accurately the image analysis device can execute the image analysis.

The technique disclosed herein can be applied to an image analysis method. Moreover, a control method, a computer program and a non-transitory computer-readable medium storing the computer program for implementing the above image analysis device are also novel and useful.

BRIEF DESCRIPTION OF DRAWINGS

(Configuration of Image Analysis Device: FIG. 1). FIG. 1 shows a configuration of an image analysis device 10. The image analysis device 10 is provided with an operation unit 12, a display unit 14, an input unit 16, and a controller 30. The respective units 12 to 30 are connected to a bus line (reference sign omitted). The operation unit 12 is provided with a mouse and a keyboard, for example. A user can provide various instructions to the image analysis device 10 by operating the operation unit 12. The display unit 14 is a display configured to display various types of information.

Figure 1:
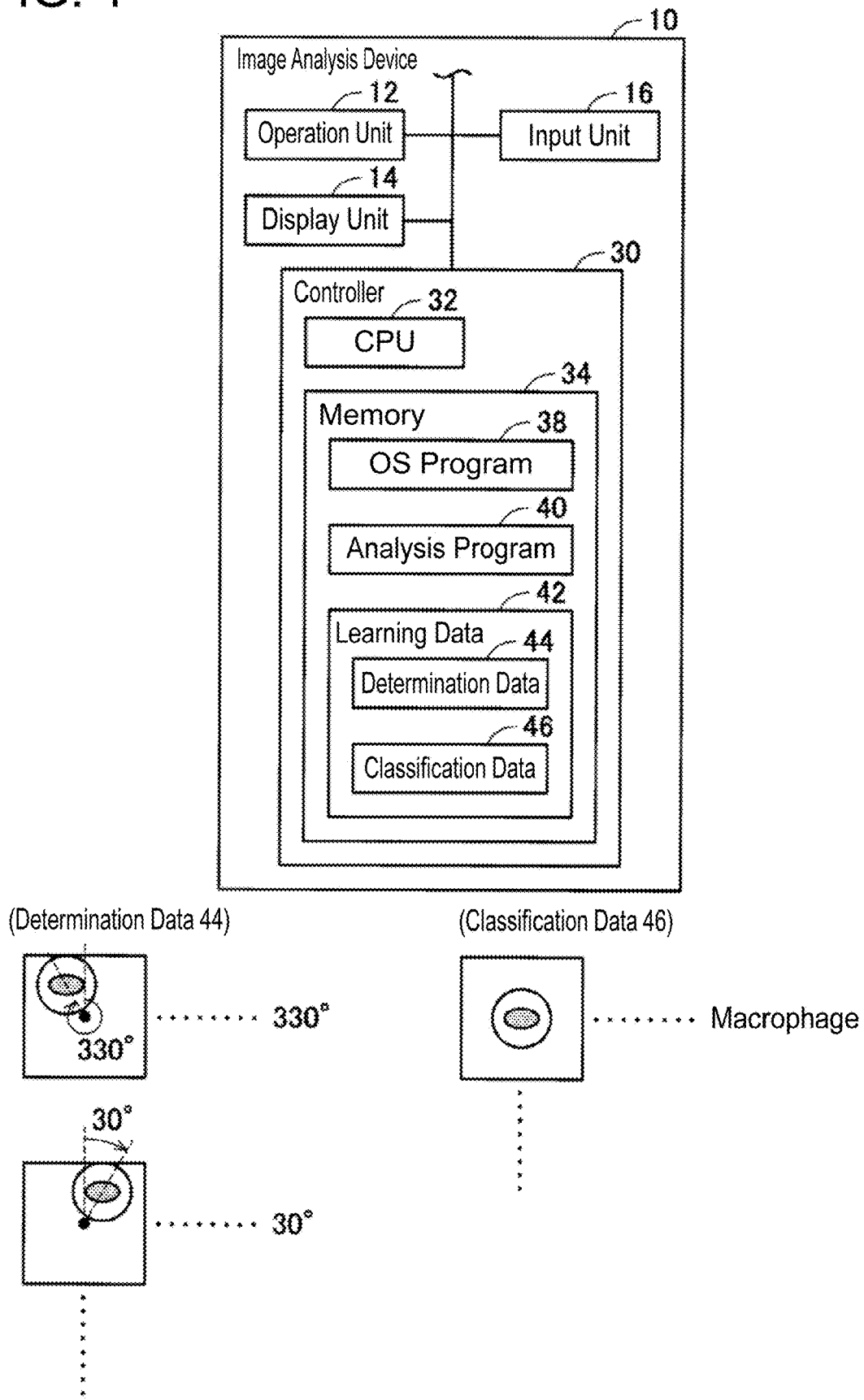
FIG. 1 shows a block diagram of an image analysis device.

The input unit 16 is a device configured to input cell image data that represents a cell image including a plurality of cell objects to the image analysis device 10. The input unit 16 may be a communication interface configured to execute wired or wireless communication, or a memory interface to which a USB memory or the like is to be inserted. For example, the input unit 16 may execute wired or wireless communication with a device that stores cell image data captured by a microscope, a Whole Slide Image, or a virtual side, and may receive the cell image data from this device, by which the cell image data may be inputted to the image analysis device 10. Further, for example, the input unit 16 may read out cell image data from a memory storing the cell image data, by which the cell image data may be inputted to the image analysis device 10.

The controller 30 is provided with a CPU 32 and a memory 34. The CPU 32 is configured to execute various processes according to programs 38, 40 stored in the memory 34. The memory 34 stores an OS program 38 for realizing basic operations of the image analysis device 10 and an analysis program 40 for executing image analysis according to a convolutional neural network (hereinbelow termed "CNN (abbreviation of Convolutional Neural Network)"). For example, the image analysis device 10 is realized by installing the analysis program 40 to a general-purpose PC or a server. The analysis program 40 may execute image analysis according to a large-scale network (such as GoogLeNet (registered trademark), Residual Network) that includes CNN as its partial structure. Further, the memory 34 stores learning data 42 for executing image analysis according to the analysis program 40. The learning data 42 may be provided by a vendor who sells the analysis program 40, or may be generated by the user of the image analysis device 10. In the former case, the learning data 42 is stored in the memory 34 upon installation of the analysis program 40. In the latter case, the learning data 42 is stored in the memory 34 by the user of the image analysis device 10 after installation of the analysis program 40.

The learning data 42 includes determination data 44 for determining whether a center of an analysis target image matches a center of a cell object, and classification data 46 for classifying a cell corresponding to the cell object. The determination data 44 is data in which image data is associated with a center position of a cell object included in an image represented by the image data for each of a plural pieces of image data. The center position is expressed in a phase (that is, an angle) of the cell object in the present embodiment, however, it may be expressed in coordinates in a variant. The classification data 46 is data in which image data is associated with a type of cell object included in the image represented by the image data for each of the plural pieces of image data.

Figure 2:
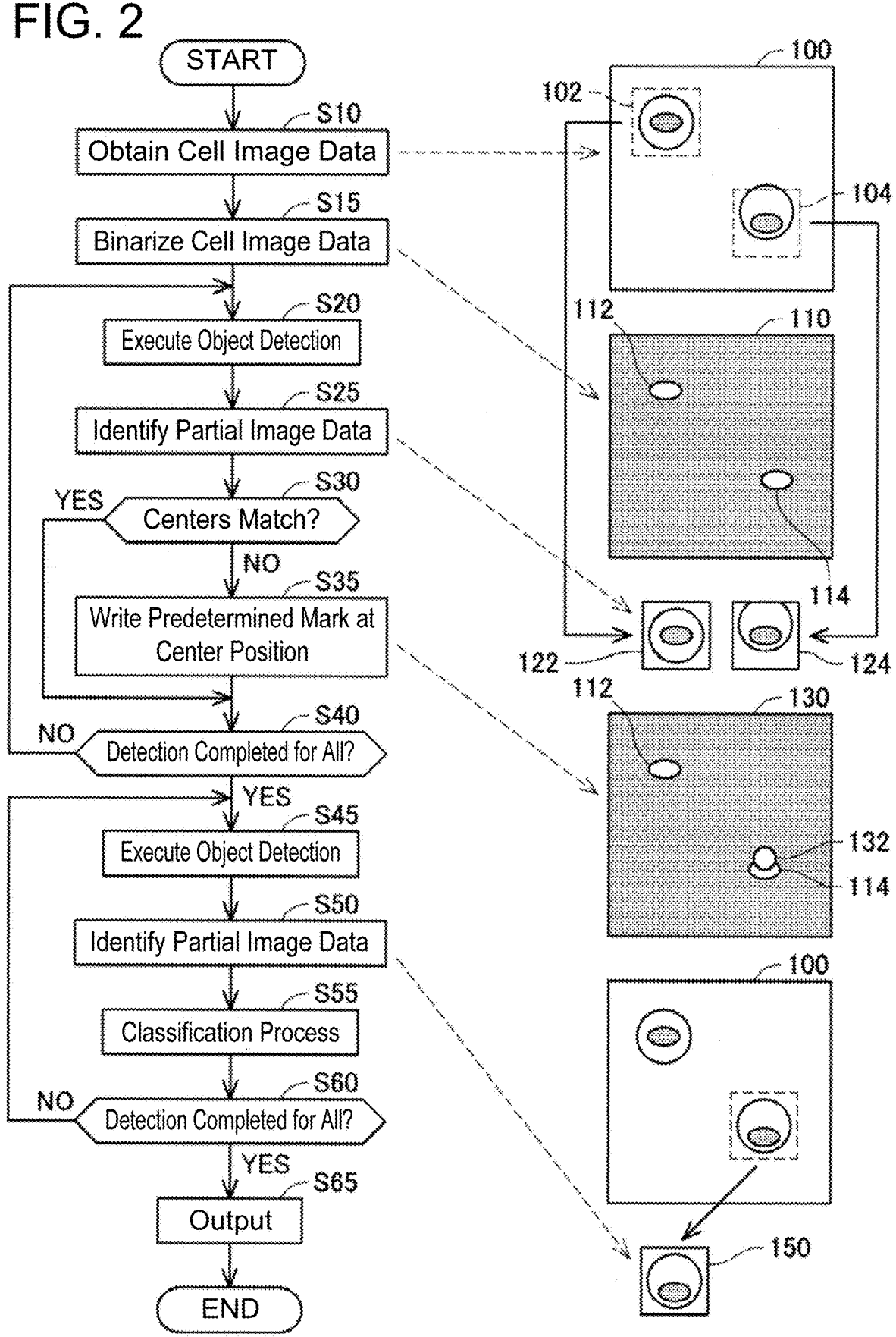
FIG. 2 shows a flowchart of a process which the image analysis device executes.

(Process of Image Analysis Device 10: FIG. 2). Next, a process which the CPU 32 of the image analysis device 10 executes according to the analysis program 40 will be described with reference to FIG. 2. In S10, the CPU 32 obtains cell image data that represents a cell image 100 including a plurality of cell objects 102, 104, via the input unit 16. The cell image data is bitmap data constituted of a plurality of pixels having multilevel RGB values (e.g., 256 levels). A file format of the bitmap data is not limited to BMP (Microsoft Windows (registered trademark) Bitmap Image), and may be JPEG (Joint Photographic Experts Group), TIFF (Tagged Image File Format), or the like. The cell image data may be generated as described below. For example, bronchioalveolar lavage fluid, which is a specimen collected from a patient, is applied to a slide glass and Giemsa stain is performed thereon to produce a pathological specimen. Then, the pathological specimen is captured by a microscope to generate cell image data. The pathological specimen is not limited to the above. For example, the specimen may be a blood specimen, a biological specimen, or the like, and the stain method may be a Papanicolaou stain method, a hematoxylin and eosin stain method, an immunohistochemistry stain method, or an immunofluorescence stain method. Further, an unstained phase-contrast microscopic image of cultured cells may be used.

In S15, the CPU 32 binarizes the cell image data obtained in S10. Specifically, for each of the plurality of pixels constituting the cell image data, the CPU 32 calculates a luminance value from the RGB value of the pixel (e.g., luminance value $Y=0.299\times R+0.587\times G+0.114\times B$), and then determines that a pixel value of the pixel is "1" in a case where the luminance value is greater than a threshold (such as 127), while determines that the pixel value of the pixel is "0" in a case where the luminance value is equal to or less than the threshold. By doing so, the CPU 32 generates binary image data constituted of a plurality of pixels each having "1" or "0". Hereinbelow, a pixel having the pixel value "1" and a pixel having the pixel value "0" are respectively termed an "ON pixel" and an "OFF pixel". FIG. 2 shows a binary image 110 represented by the binary image data, and in the binary image 110, the ON pixels are expressed in white and the OFF pixels are expressed in black. As a result, an ON pixel group 112 indicating a portion of the cell object 102 that is relatively deeply stained is expressed in white.

In S20, the CPU 32 executes object detection. Specifically, from the binary image 110 represented by the binary image data generated in S15, the CPU 32 detects a center position (that is, coordinates) of one ON pixel group (such as 112 or 114) constituted of a predetermined number of ON pixels or more adjacent to each other as a position of a candidate object which is a candidate of cell object. In doing so, a region dividing method such as a watershed method may be used together.

In S25, the CPU 32 identifies partial image data that corresponds to the position of the candidate object detected in S20, from the cell image data. Due to this, partial image data of a target of processes of S30 and S35 to be described later (hereinbelow termed "target partial image data") is identified. Specifically, the CPU 32 identifies the target partial image data, which represents a rectangular image having a predetermined size of which center is the position (that is, the coordinates) detected in S20, from the cell image data. In the example of FIG. 2, the CPU 32 identifies target partial image data representing a partial image 122 from the cell image data in a case of having detected the position of the ON pixel group 112 in S20, while the CPU 32 identifies target partial image data representing a partial image 124 from the cell image data in a case of having detected the position of the ON pixel group 114 in S20.

In S30, the CPU 32 executes a center determination process on the target partial image data by using the determination data 44 included in the learning data 42. The center determination process includes determining whether a center of a partial image represented by target partial image data (hereinbelow termed a "target partial image") matches a center of cell object. Specifically, in a case where a phase of cell object (such as 30° in FIG. 1) included in a target partial image can be identified by executing CNN using the determination data 44, the CPU 32 determines that the center of the target partial image does not match the center of the cell object (NO in S30) and proceeds to S35. On the other hand, in a case where a phase of cell object included in a target partial image cannot be identified, the CPU 32 determines that the center of the target partial image matches the center of the cell object (YES in S30), skips S35 and proceeds to S40. For example, since the cell object is located at the center in the partial image 122, it is determined that the center of the partial image 122 matches the center of the cell object (YES in S30). Further, for example, since the cell object is located not at the center but at the upper portion in the partial image 124, it is determined that the center of the partial image 124 does not match the center of the cell object (NO in S30).

In S35, the CPU 32 writes a predetermined mark in the binary image 110. Specifically, the CPU 32 firstly identifies the phase of cell object, which is the determination result of S30, as a center position of the cell object in the target partial image. Then, the CPU 32 changes the binary image data by writing the predetermined mark at a position corresponding to the identified center position (that is, the identified phase) in the binary image 110. The predetermined mark has a shape that can be detected in object detection of S45 to be described later, and in this embodiment, it is a circular mark having a white center portion and a black peripheral portion. In the example of FIG. 2, the CPU 32 generates binary image data representing a changed binary image 130 by writing a predetermined mark 132 in the binary image 110. In a variant, the predetermined mark is not limited to the circular mark, and may have a rectangular shape or another shape.

In S40, the CPU 32 determines whether the detection (that is, S20) has been completed for all objects within the binary image 110. The CPU 32 proceeds to S45 in a case of determining that the detection has been completed for all the objects (YES in S40), while the CPU 32 returns to S25 in a case of determining that the detection has not been completed yet for all the objects (NO in S40).

S45 and S50 are the same as S20 and S25 except that the changed binary image data is used. Since the mark 132 is written in S35 as above, the CPU 32 can identify in S50 partial image data representing a partial image 150 that is a rectangular image having the mark 132 located at a center thereof. That is, in this partial image data, the center of the partial image 150 matches the center of the cell object. Since the predetermined mark has the black peripheral portion as described above, it is not integrated with other objects. Due to this, the CPU 32 can correctly detect the mark 132.

In S55, the CPU 32 executes CNN using the partial image data identified in S50 and the classification data 46 to classify the cell that corresponds to the cell object included in the partial image represented by the partial image data. Since the center of the partial image 150 matches the center of the cell object as described above, the CPU 32 can accurately classify the cell corresponding to this cell object.

S60 is the same as S40. The CPU 32 proceeds to S65 in a case of determining that the detection has been completed for all the objects (YES in S60), while the CPU 32 returns to S45 in a case of determining that the detection has not been completed yet for all the objects (NO in S60).

In S65, the CPU 32 outputs a classification result of S55. Specifically, the CPU 32 causes the display unit 14 to display the classification result. The classification result may, for example, be information including a number of target cells, information including numbers of classified cells by types thereof, or a score indicating expression of a specific protein in the cell. Further, it may be a grade of malignancy or an expression level of gene mutation predicted from the cell classification result, or a prediction of prognosis of the patient. Results of the center determination process of S30 and the classification process of S55 may be added to the determination data 44 and the classification data 46. By doing so, accuracy of CNN can be improved.

(Details of Processes of S30 and S35 in FIG. 2; FIGS. 3 and 4). Next, details of the processes of S30 and S35 in FIG. 2 will be described with reference to FIGS. 3 and 4. FIG. 3 shows examples of partial image identified in S25 of FIG. 2. FIG. 4 shows positions and shapes of the predetermined mark written in S35 according to the center positions of cell objects. Further, FIG. 4 also shows the phases indicating the center positions of cell objects.

Figure 3A:
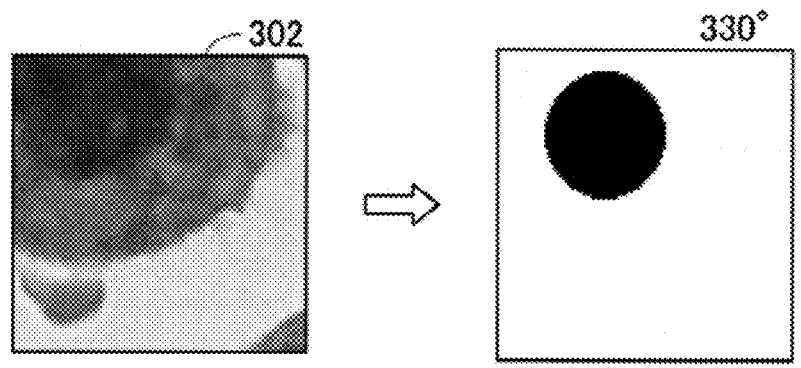
FIGS. 3A to 3E show various cell objects and center positions thereof.
Figure 4A:
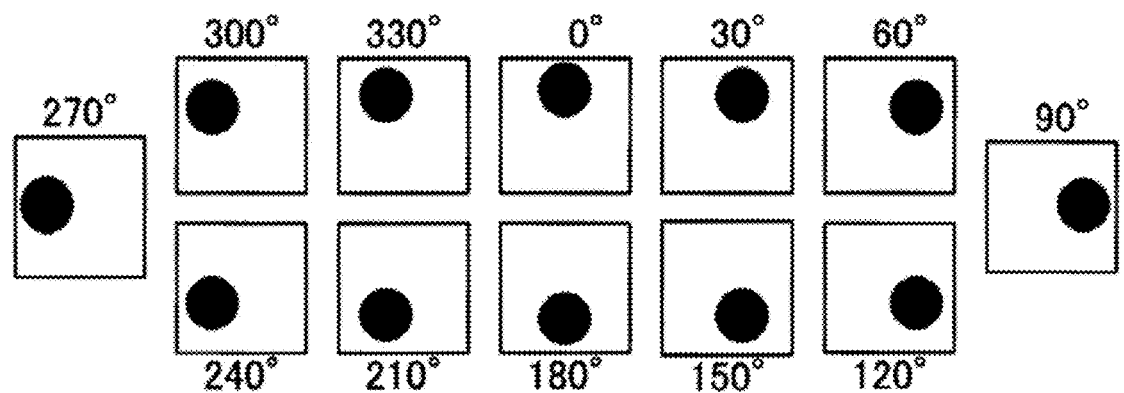
FIGS. 4A to 4D show positions and shapes of predetermined marks corresponding to the center positions.

A partial image 302 of FIG. 3A includes a cell object corresponding to one macrophage. The center of the partial image 302 does not match the center of the cell object, and thus 330° is identified in S30 as the center position of the cell object. Then, in S35, the position and shape of the predetermined mark corresponding to the phase 330° in FIG. 4A are identified, and the predetermined mark having the identified shape (that is, the circular mark having the black peripheral portion) is written at a position in the binary image corresponding to the identified position.

Figure 3B:
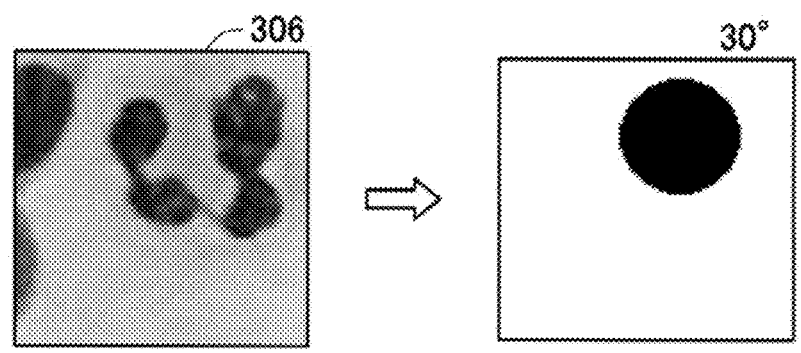

A partial image 306 of FIG. 3B includes a cell object corresponding to one neutrophil. Since neutrophils include segmented nuclei, it had been difficult to correctly identify the centers of neutrophils by conventional image analyses. In the present embodiment, the determination data 44 includes data in which image data that represents an image including a cell object corresponding to a neutrophil is associated with a center position of this cell object. Due to this, 30° is identified in S30 as the center position of the cell object, and the predetermined mark according to the position and shape corresponding to the phase 30° in FIG. 4A is written in S35. As a result, in the partial image data identified in S50, the center of a partial image represented by this partial image data matches the center of the cell object corresponding to the neutrophil. Due to this, the neutrophil can accurately be classified in S55 based on this partial image data.

Figure 3C:
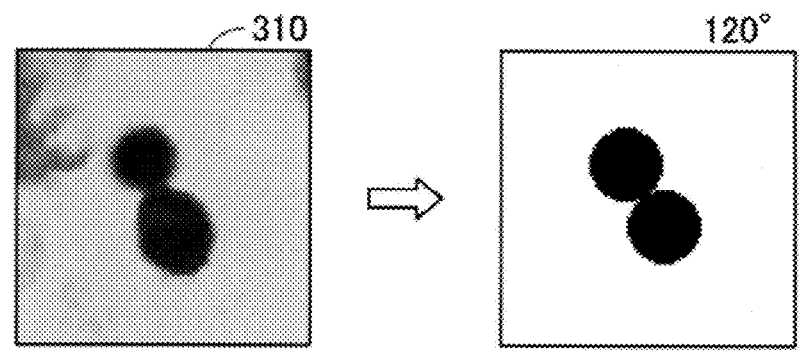
Figure 4B:
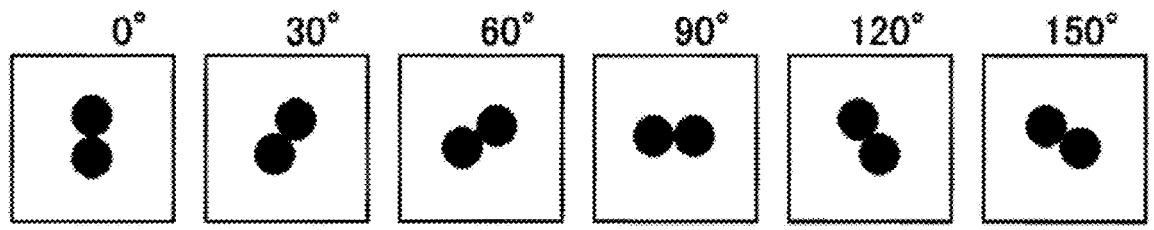

A partial image 310 of FIG. 3C includes two cell objects corresponding to two adjacent lymphocytes. Conventional image analyses divide each of such two or more cells by a region dividing method and classify them, however, they may fail to divide the cells correctly. In the present embodiment, the determination data 44 includes data in which image data that represents an image including two cell objects corresponding to two lymphocytes is associated with center positions of these two cell objects. Due to this, 120° is identified in S30 as the center positions, and two predetermined marks according to the position and shape corresponding to phase 120° in FIG. 4B are written in S35. As a result, the respective positions of the two predetermined marks are detected in S45. Accordingly, partial image data corresponding to the position of one of the predetermined marks is identified in S50 (that is, the center of the partial image matches the center of the cell object corresponding to one of the lymphocytes), and the one of the lymphocytes is classified in S55. After this, partial image data corresponding to the position of the other predetermined mark is identified in S50 (that is, the center of the partial image matches the center of the cell object corresponding to the other lymphocyte), and the other lymphocytes is classified in S55. As above, even when a partial image identified in S25 includes two cell objects, each of the two cells can accurately be classified.

Figure 3D:
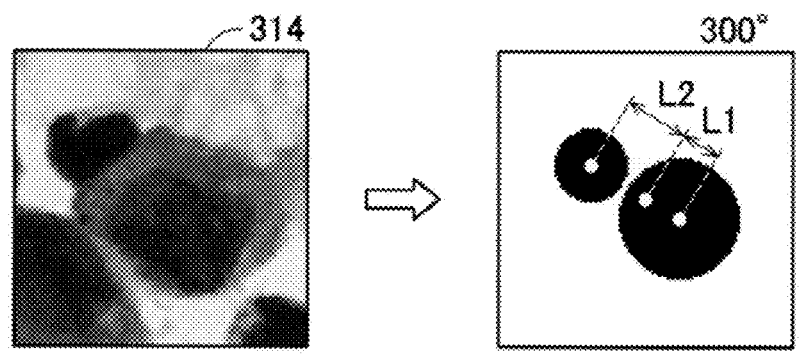
Figure 4C:
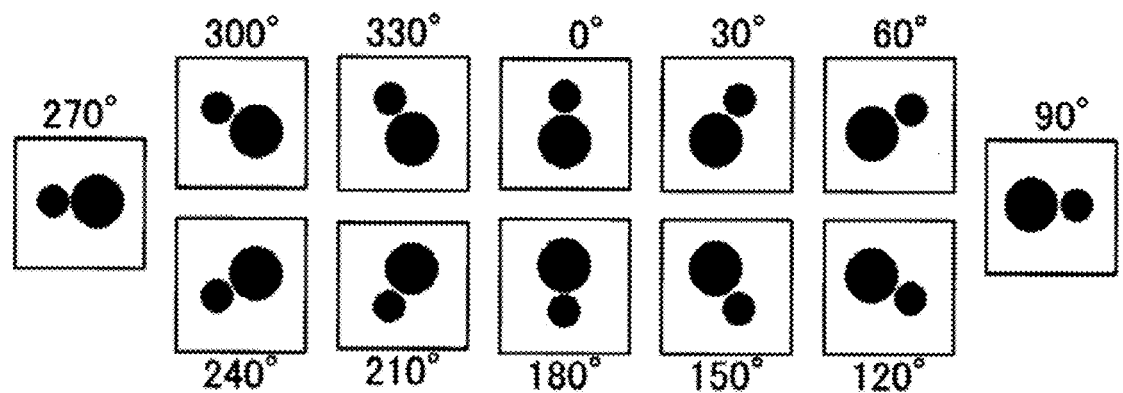

A partial image 314 of FIG. 3D includes two cell objects corresponding to a lymphocyte and a macrophage adjacent to each other. In the partial image 314, a distance L2 between the center of the partial image 314 and the center of the cell object corresponding to the lymphocyte is larger than a distance L1 between the center of the partial image 314 and the center of the cell object corresponding to the macrophage, thus the distances from the center of the partial image 314 to the respective centers of the cell objects are not constant. In the present embodiment, the determination data 44 includes data in which image data that represents an image including two cell objects corresponding to a lymphocyte and a macrophage is associated with the center positions of these two cell objects. Due to this, 300° is identified in S30 as the center positions, and two predetermined marks according to the position and shape corresponding to phase 300° in FIG. 4C are written in S35. In the present embodiment, since a size of the cell object corresponding to the macrophage is larger than a size of the cell object corresponding to the lymphocyte, the predetermined mark corresponding to the former cell object is larger than the predetermined mark corresponding to the latter cell object, as shown in FIG. 4C. However, in a variant, the two predetermined marks may have the same size. In S45, the respective positions of the two predetermined marks are detected. Thus, two pieces of partial image data according to the positions of the two predetermined marks are sequentially identified in S50, and the one lymphocyte and the one macrophage are sequentially classified in S55. As above, even when distances between the center of partial image and the centers of cell objects are different, the respective cells can accurately be classified.

Figure 3E:
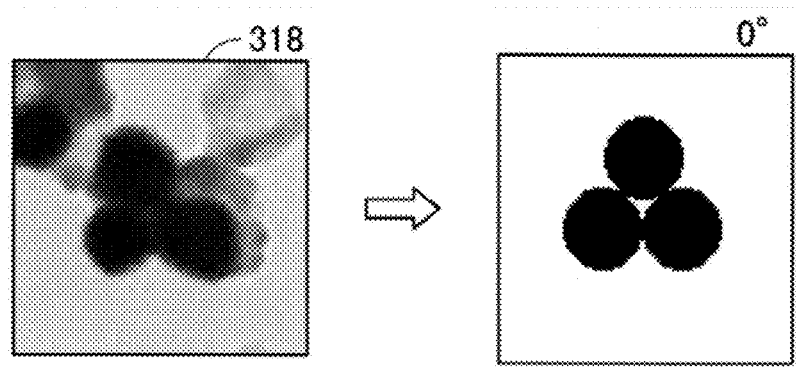
Figure 4D:
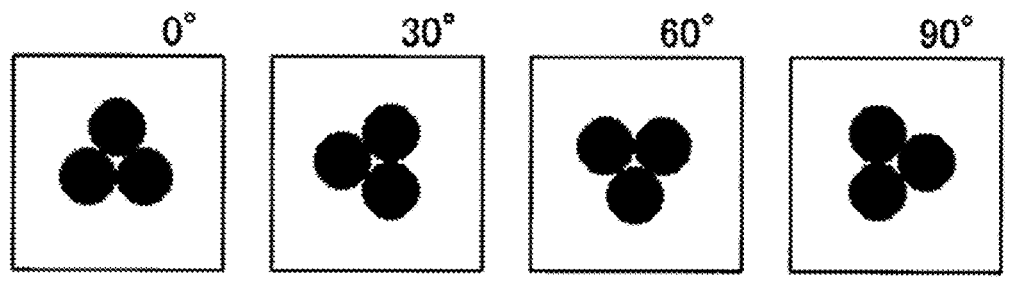

A partial image 318 of FIG. 3E includes three cell objects corresponding to three lymphocytes. In the present embodiment, the determination data 44 includes data in which image data that represents an image including three cell objects corresponding to three lymphocytes is associated with the center positions of these three cell objects. Due to this, 0° is identified in S30 as the center positions, and three predetermined marks according to the position and shape corresponding to phase 0° in FIG. 4D are written in S35. As a result, the respective positions of the three predetermined marks are detected in S45. Accordingly, three pieces of partial image data according to the positions of the three predetermined marks are sequentially identified in S50, and the three lymphocytes are sequentially classified in S55. As above, even when a partial image identified in S25 includes three cell objects, the three cells can accurately be classified. Although the present embodiment describes examples that the number of cell objects included in a partial image is up to three, however, the determination data 44 for four or more cell objects may be used in a variant.

(Case A: FIG. 5). Next, specific cases realized by the process of FIG. 2 will be described with reference to FIGS. 5 to 7. FIG. 5 shows diagrams for explaining Case A in which cell image data that is obtained from a blood smear prepared by executing Giemsa stain on bone marrow blood is inputted to the image analysis device 10.

Figure 5A:
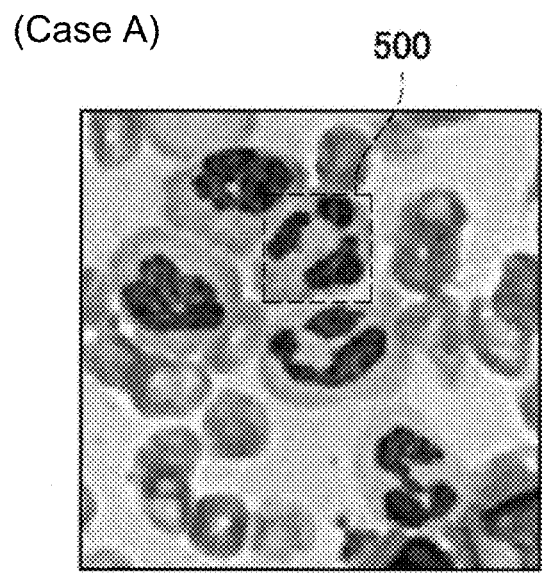
FIGS. 5A to 5D show Case A of analyzing a pathological specimen corresponding to bone marrow blood.
Figure 5B:
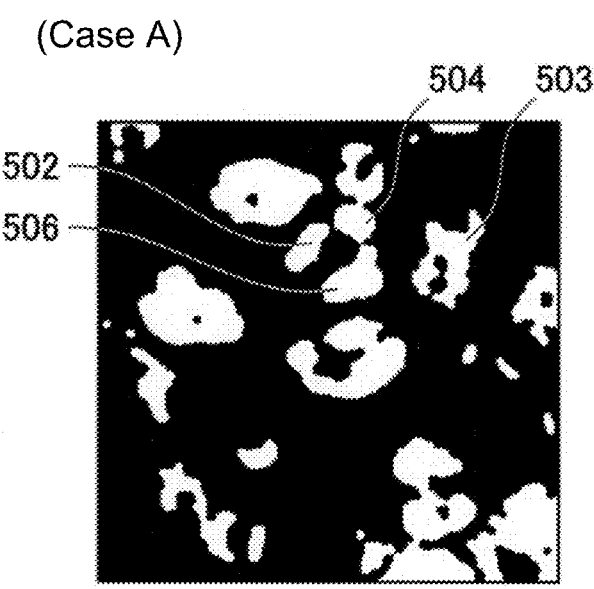
Figure 5C:

FIG. 5A shows a cell image obtained in S10. A sign 500 shows a cell object corresponding to one neutrophil. FIG. 5B shows a binary image generated in S15. The image analysis device 10 uses the binary image of FIG. 5B to execute a first round of object detection (S20). In doing so, a region dividing method such as a watershed method is used. As a result, for example, three candidate objects 502, 504, 506 are identified sequentially for the cell object 500. As a result, the identification of partial image data (S25), the determination that the center of the partial image does not match the center of the cell object (NO in S30), and the writing of marks 507, 508, 509 to the binary image (S35) are executed for each of the three candidate objects 502, 504, 506. FIG. 5C shows a changed binary image obtained by a plurality of marks including the marks 507, 508, 509 being written. In this example, positions of the three marks 507, 508, 509 overlap. In such a situation, the mark 508, which was written last, is brought to the foreground in the present embodiment. In a variant, a mark that is highly likely the center of a cell object may be identified, and this mark may be brought to the foreground.

A sign 503 in FIG. 5B is also identified as a candidate object (S20). In this case, in the center determination process for partial image data identified for the candidate object 503, it is determined that the partial image does not include a cell object corresponding to a neutrophil which is the analysis target cell of the present case. As a result, NO is determined in S30, however, no mark is written in S35 (this case is omitted from FIG. 2).

Figure 5D:
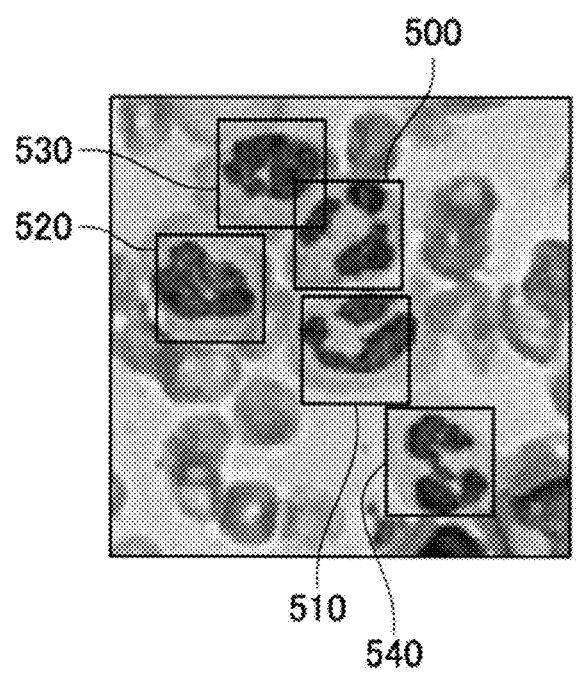

The image analysis device 10 uses the changed binary image of FIG. 5C to execute a second round of object detection (S45). As a result, for example, the mark 508 is detected as a candidate object for the cell object 500. As a result, partial image data having a center that matches the center of the cell object 500 is identified in S50, and the neutrophil corresponding to the cell object 500 is classified in S55. The image analysis device 10 executes the same processes to cell objects other than the cell object 500, as a result of which a plurality of cells corresponding to a plurality of cell objects 510 to 540 can accurately be classified, as shown in FIG. 5D.

As described above, in the case of sequentially identifying the three candidate objects 502, 504, 506 in the first round of object detection, the image analysis device 10 sequentially writes the three marks 507, 508, 509. Here, as a comparative example, it is considered to employ a configuration in which the image analysis device 10 sequentially identifies three pieces of partial image data corresponding to the positions of the three marks 507, 508, 509 from the cell image data, instead of writing the three marks 507, 508 and 509, and sequentially classifies the cells by using the three pieces of partial image data. However, according to the configuration of the comparative example, the three pieces of partial image data including the same cell are sequentially identified and thus the same cell is classified three times. Contrary to this, in the present embodiment, the image analysis device 10 writes the three marks 507, 508, 509 such that the mark 508 is brought to the foreground. Due to this, the image analysis device 10 can detect the mark 508 in the second round of object detection without detecting the marks 507, 509 which do not have sufficient areas for object detection, and classify the cell using the partial image data corresponding to the mark 508. Due to this, the unnecessity that three pieces of partial image data including the same cell are sequentially identified and the same cell is classified three times can be eliminated. However, in a variant, the configuration of the above-described comparative example may be employed.

(Case B: FIG. 6). Next, specific Case B will be described with reference to FIG. 6. In Case B, cell image data that is obtained from a pathological specimen prepared by executing hematoxylin and eosin stain on a gastric tissue specimen is inputted to the image analysis device 10.

Figure 6A:
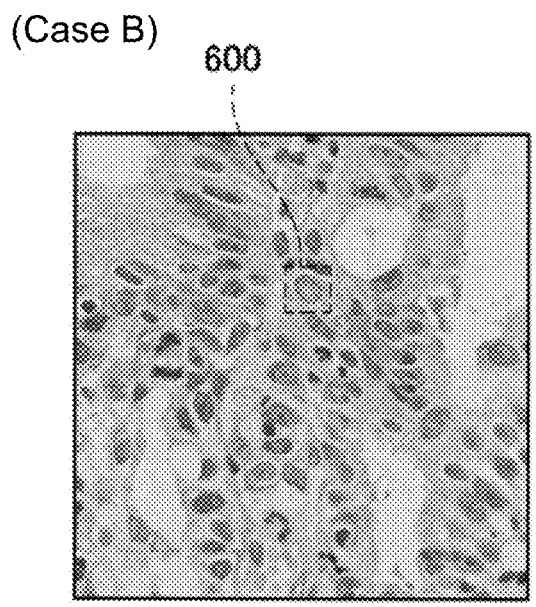
FIGS. 6A to 6D show Case B of analyzing a pathological specimen corresponding to a gastric tissue specimen.
Figure 6B:
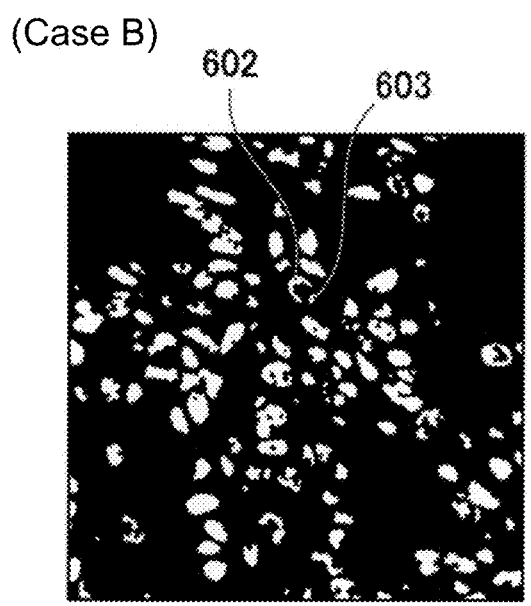
Figure 6C:
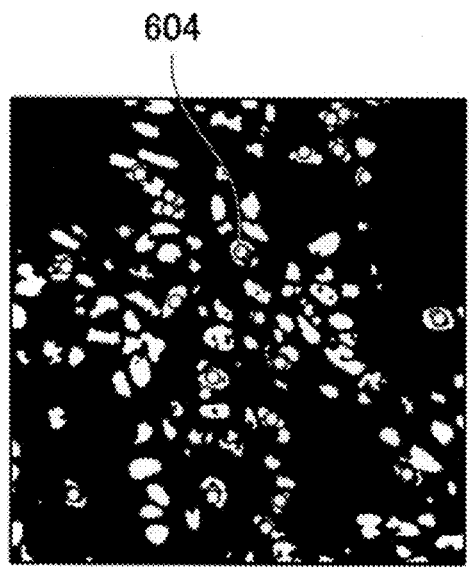
Figure 6D:
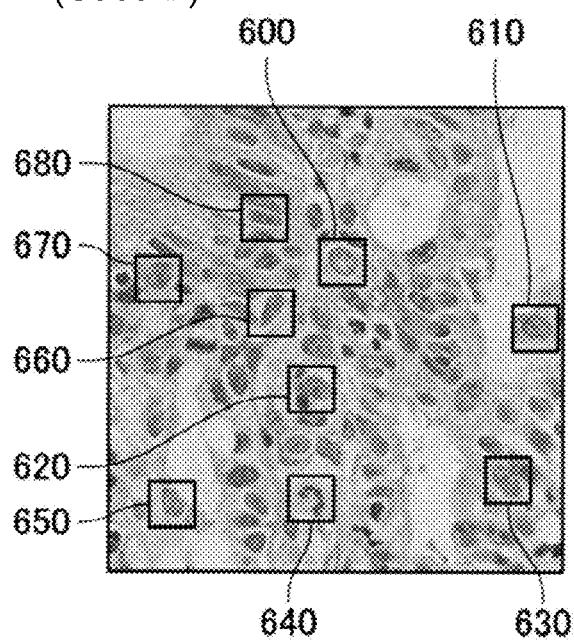

FIG. 6A shows a cell image obtained in S10, and a sign 600 shows a cell object corresponding to one cancer cell. FIG. 6B shows a binary image generated in S15. In a cancer cell, its nucleus may not be stained uniformly and only an edge of the nucleus may be stained in a dark tone. Due to this, in the first round of object detection (S20), two candidate objects 602, 603 are identified sequentially for the cell object 600. As a result, the image analysis device 10 writes two marks corresponding to the two candidate objects 602, 603 (S35). FIG. 6C shows a changed binary image. Although the positions of the aforementioned two marks overlap, a sign is given only to a mark 604 which was written last. The image analysis device 10 uses the changed binary image to execute the second round of object detection (S45), identifies partial image data having a center that matches the center of the cell object 600 (S50), and classifies the cancer cell corresponding to the cell object 600 (S55). The image analysis device 10 executes the same processes to cell objects other than the cell object 600, as a result of which a plurality of cells corresponding to a plurality of cell objects 610 to 680 is classified, as shown in FIG. 6D.

(Case C: FIG. 7). Next, specific Case C will be described with reference to FIG. 7. In Case C, cell image data that is obtained from a pathological specimen prepared by executing immunohistochemistry stain using anti-PD-L1 antibodies on an epithelial tissue specimen is inputted to the image analysis device 10. PD-L1 is a protein expressed on a cell membrane and is expressed on macrophages and cancer cells (in particular, squamous cancer cells).

Figure 7A:
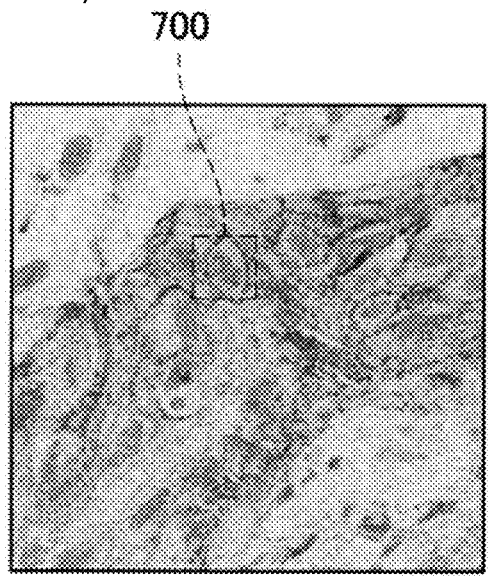
FIGS. 7A to 7D show Case C of analyzing a pathological specimen corresponding to an epithelial tissue specimen.
Figure 7B:
Figure 7C:
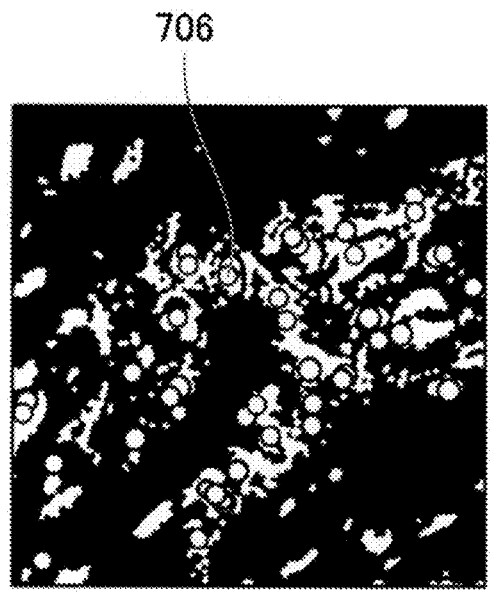
Figure 7D:
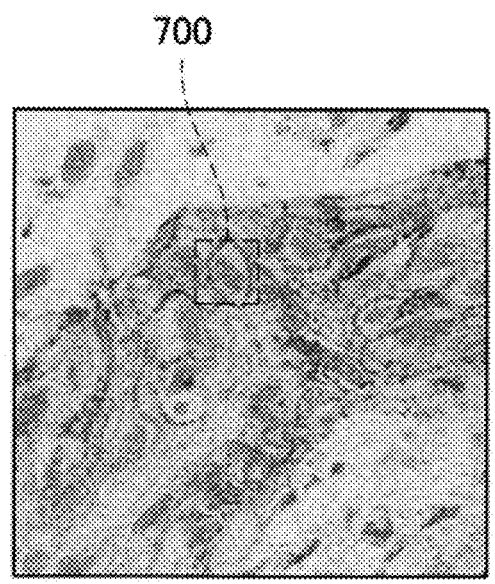

FIG. 7A shows a cell image obtained in S10, and a sign 700 shows a cell object corresponding to one squamous cancer cell having PD-L1 expressed on its cell membrane. In the immunohistochemistry stain, when a protein is expressed on a cell membrane, the stained cell membrane may be detected as a candidate object in the object detection. FIG. 7B shows a binary image generated in S15. Since the cell membrane is stained in the cell object 700, two candidate objects 702, 704 are identified sequentially in the first round of object detection (S20). As a result, the image analysis device 10 writes two marks corresponding to the two candidate objects 702, 704 (S35). FIG. 7C shows a changed binary image. Although the positions of the aforementioned two marks overlap, a sign is given only to a mark 706 which was written last. The image analysis device 10 uses the changed binary image to execute the second round of object detection (S45), identifies partial image data having a center that matches the center of the cell object 700 (S50), and classifies the squamous cancer cell corresponding to the cell object 700 (S55).

Cases A to C described above are examples of specific cases, and the image analysis device 10 may be adapted to leucocyte count in peripheral blood, classification of cells in other celomic fluids (such as pleural fluid, ascites fluid), cervical cytology, aspiration biopsy cytology for thyroid and mammary glands, and the like. Moreover, it may be adapted to classification of unstained cultured cells observed by using a phase-contrast microscope.

(Corresponding Relationships). The process of S10 and the process of S15 are respectively examples of processes executed by "obtaining unit" and "generating unit". The processes of S20 and S25 are an example of processes executed by "first image identifying unit". The process of S30 is an example of processes executed by "determining unit" and "position identifying unit". The process of S35 is an example of a process executed by "changing unit". The processes of S45 and S50 are an example of processes executed by "second image identifying unit". The process of S55 and the process of S65 are respectively examples of processes executed by "classifying unit" and "output unit".

The partial image 124 and the partial image 150 of FIG. 2 are respectively examples of "first partial image" and "second partial image". The lymphocyte and the macrophage in the partial image 314 of FIG. 3D are respectively examples of "first cell object" and "second cell object", and the distance L1 and the distance L2 are respectively examples of "first distance" and "second distance".

Figure 8:
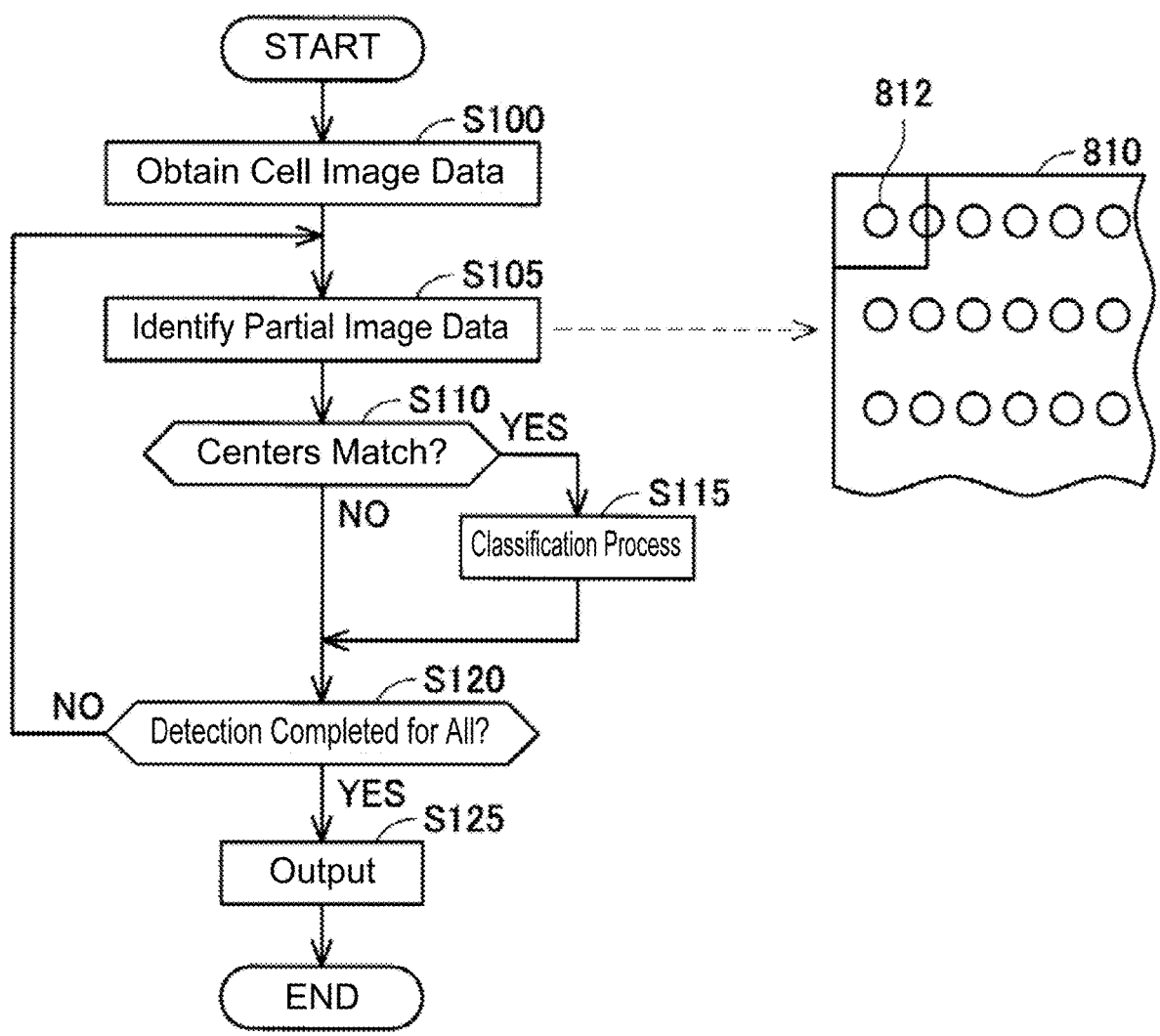
FIG. 8 shows a flowchart of a second embodiment.

(Second Embodiment; FIG. 8). In the present embodiment, the CPU 32 executes a process of FIG. 8, instead of the process of FIG. 2, according to the analysis program 40. S100 is the same as S10 of FIG. 2. In S105, the CPU 32 identifies partial image data representing partial images that are obtained by scanning a cell image represented by the cell image data obtained in S100 in a matrix pattern with a predetermined interval. Specifically, the CPU 32 determines a plurality of coordinates (such as a sign 812) in the cell image at the predetermined interval as shown in a cell image 810, and identifies the partial image data representing the partial images each of which is a rectangular image of a predetermined size having the coordinates as its center. As above, since the partial image data is identified in the matrix pattern without execution of the object detection from binary image data in the present embodiment, the process of generating binary image and the like can be omitted and processing load can thereby be reduced.

S110 is the same as S30 of FIG. 2 except that target partial image data which is a target of the center determination process is the partial image data identified in S105. In a case of determining that the center of the target partial image matches the center of a cell object (YES in S110), the CPU 32 classifies the cell similarly to S55 of FIG. 2. On the other hand, in a case of determining that the center of the target partial image does not match the center of the cell object (NO in S110), the CPU 32 does not execute S115 (that is, does not execute the classification) and proceeds to S120. In S120, the CPU 32 determines whether the identification of partial image data has been completed for all the determined coordinates in the cell image. The CPU 32 proceeds to S125 in a case of determining that the identification has been completed (YES in S120), while the CPU 32 returns to S105 in a case of determining that the identification has not been completed yet (NO in S120). S125 is the same as S65 of FIG. 2.

(Specific Case: FIG. 9). Next, a specific case realized by the process of FIG. 8 will be described with reference to FIG. 9. In the present case, cell image data that is obtained from a blood smear prepared by executing Giemsa stain on bone marrow blood is inputted to the image analysis device 10.

Figure 9A:
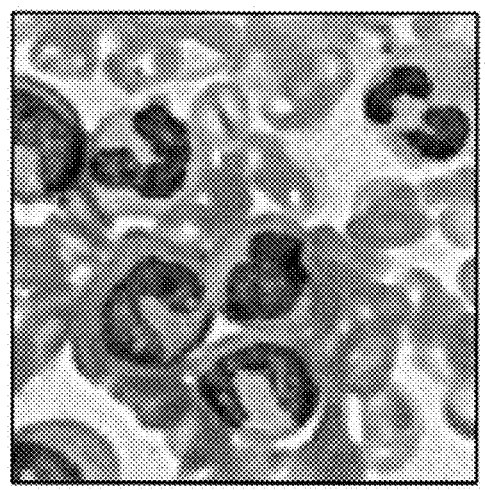
FIGS. 9A to 9B show a specific case of the second embodiment.
Figure 9B:
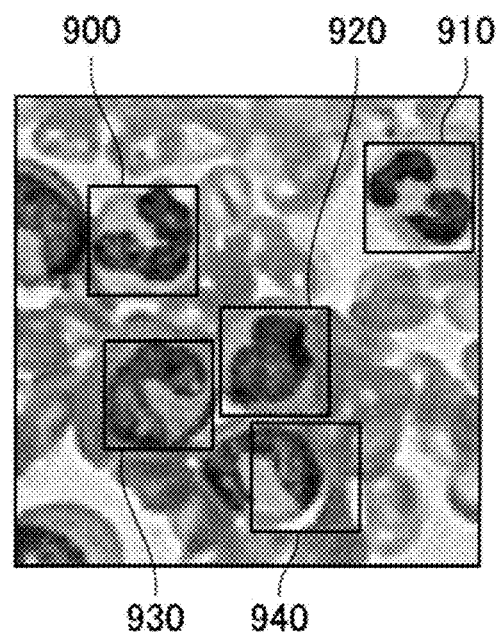

FIG. 9A shows a cell image obtained in S100. The image analysis device 10 sequentially identifies plural pieces of partial image data (S105). As a result, for example, plural partial images including five partial images 900 to 940 of FIG. 9B are sequentially identified, and the center determination process is executed for each of the partial images (S110). For each of the four partial images 900 to 930, it is determined that the center of the partial image matches the center of cell object (YES in S110), as a result of which cells corresponding to the cell objects included in the partial images are classified (S115). On the other hand, for the partial image 940, it is determined that the center of this partial image does not match the center of cell object (NO in S110), and the classification therefor is not executed. Due to this, erroneous cell classification can be suppressed.

(Corresponding Relationships). The process of S100, the process of S105, the process of S110, the process of S115, and the process of S125 are respectively examples of processes executed by "obtaining unit", "first image identifying unit", "determining unit", "classifying unit", and "output unit".

Figure 10:
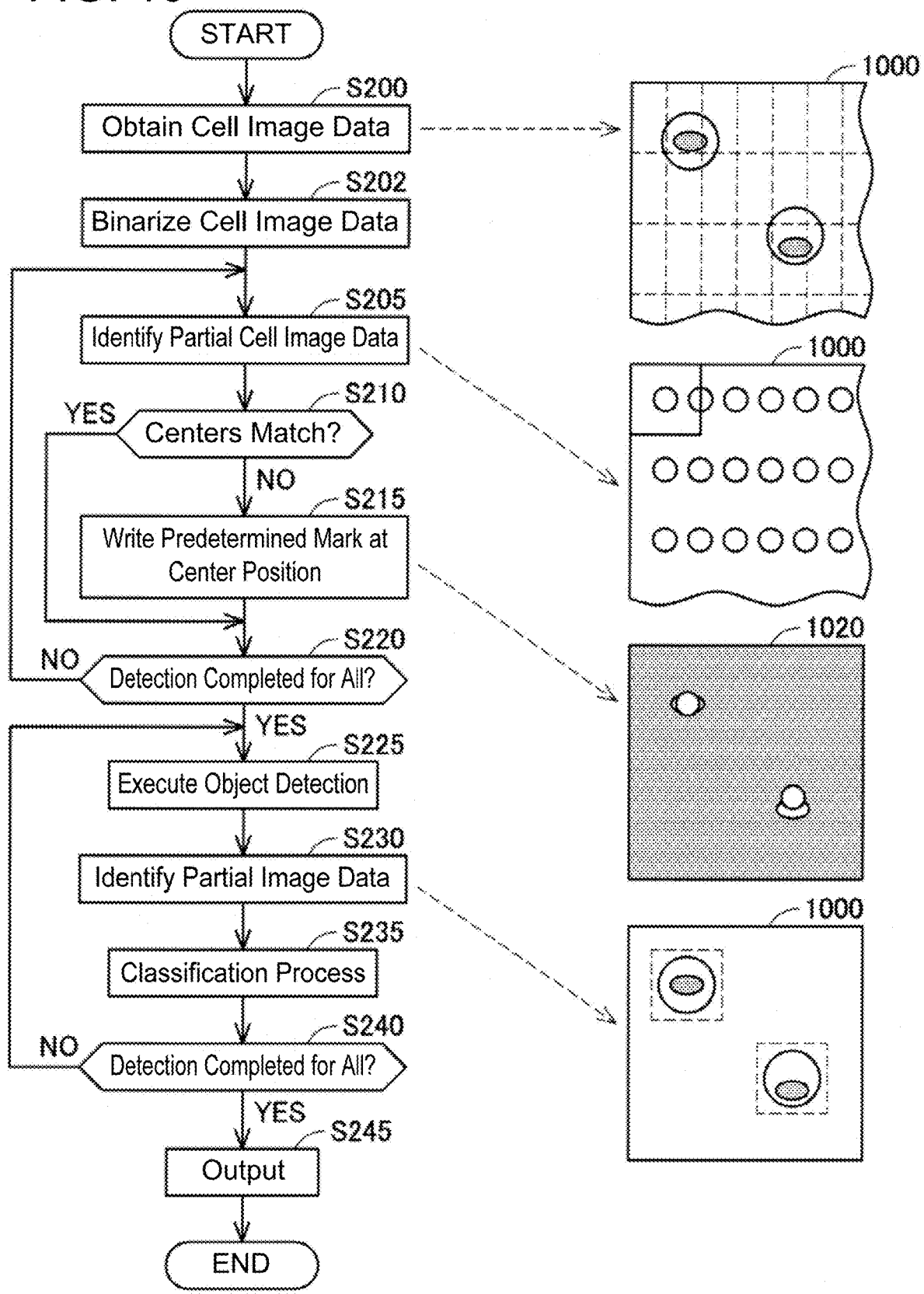
FIG. 10 shows a flowchart of a third embodiment.

(Third Embodiment; FIG. 10). In the present embodiment, the CPU 32 executes a process of FIG. 10, instead of the process of FIG. 2, according to the analysis program 40. S200 and S202 are the same as S10 and S15 of FIG. 2. S205 is the same as S105 of FIG. 8. Topmost rectangles indicated by broken lines in a cell image 1000 of FIG. 10 show partial images sequentially identified in S205. S210 is the same as S30 of FIG. 2. The CPU 32 proceeds to S215 in a case of determining that the center of a target partial image does not match the center of cell object (NO in S210), while the CPU 32 skips S215 and proceeds to S220 in a case of determining that the center of the target partial image matches the center of cell object (YES in S210). S215 is the same as S35 of FIG. 2. In this example of FIG. 10, the CPU 32 generates changed binary image data representing a changed binary image 1020 by writing two marks. S220 is the same as S120.

S225 and S230 are the same as S20 and S25 of FIG. 2. Lowermost rectangles indicated by broken lines in the cell image 1000 of FIG. 10 show partial images sequentially identified in S230. S235 to S245 are the same as S55 to S65.

Figure 11A:
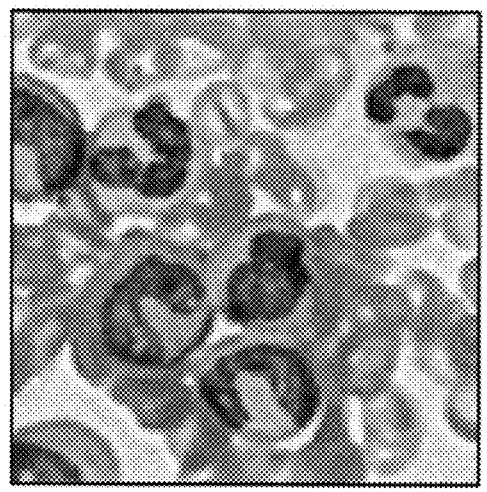
FIGS. 11A to 11C show a specific case of the third embodiment.
Figure 11B:
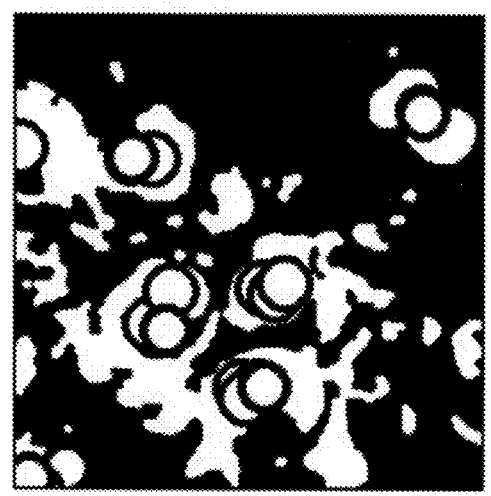
Figure 11C:
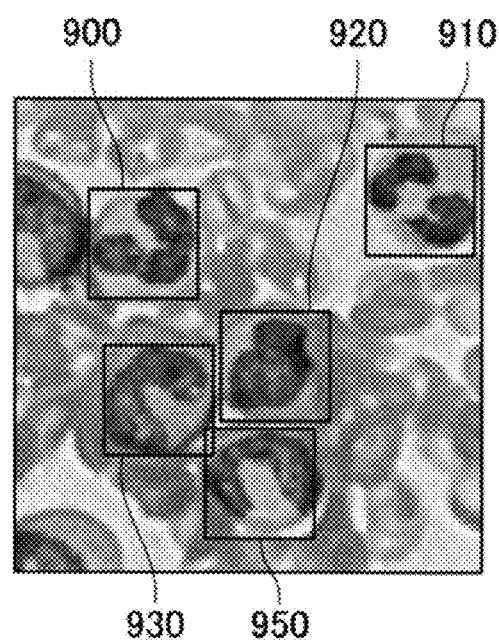

(Specific Case: FIG. 11). Next, a specific case realized by the process of FIG. 10 will be described with reference to FIG. 11. In the present case, cell image data that is the same as that of FIG. 9 is inputted to the image analysis device 10. FIG. 11A is the same as FIG. 9A. When the processes of S205 to S220 are executed on a cell image of FIG. 11A, a changed binary image of FIG. 11B is obtained. When S225 and S230 are executed using this changed binary image, partial images 900 to 950 corresponding to the positions of marks are identified as shown in FIG. 11C. In each of the partial images 900 to 950, the center of the partial image matches the center of cell object. Due to this, each cell can accurately be classified (S235).

(Corresponding Relationships). The process of S200, the process of S202, and the process of S205 are respectively examples of processes executed by "obtaining unit", "generating unit", and "first image identifying unit". The process of S210 is an example of a process executed by "determining unit" and "position identifying unit". The process of S215 and the process of S245 are respectively examples of processes executed by "changing unit" and "output unit". The processes of S225 to S235 are an example of processes executed by "classifying unit".

Specific examples of the present disclosure have been described in detail, however, these are mere exemplary indications and thus do not limit the scope of the claims. The art described in the claims include modifications and variations of the specific examples presented above.

Moreover, technical features described in the description and the drawings may technically be useful alone or in various combinations, and are not limited to the combinations as originally claimed. Further, the art described in the description and the drawings may concurrently achieve a plurality of aims, and technical significance thereof resides in achieving any one of such aims.

REFERENCE SIGNS LIST

10: image analysis device; 12: operation unit; 14: display unit; 16: input unit; 30: controller; 32: memory; 38: OS program; 40: analysis program; 42: learning data; 44: determination data; 46: classification data; 100, 810, 1000: cell image; 102, 104, 500, 510, 520, 530, 540, 600, 610, 620, 630, 640, 650, 660, 670, 680, 700: cell object; 110, 130, 1020: binary image; 112, 114: pixel group; 132, 507, 508, 509, 604, 706: predetermined mark; 122, 124, 150, 302, 306, 310, 314, 318, 900, 910, 920, 930, 940, 950: partial image; 502, 503, 504, 506, 602, 603, 702, 704: candidate object

The invention claimed is:

1. An image analysis device comprising:
a memory that stores learning data for image analysis, the learning data including determination data and classification data, the determination data being for determining whether a center of an analysis target image matches a center of a cell object, the classification data being for classifying a cell corresponding to a cell object;
an obtaining unit configured to obtain cell image data representing a cell image including a plurality of cell objects;
a generating unit configured to generate binary image data by binarizing the cell image data;
a first image identifying unit configured to identify plural pieces of partial image data sequentially from the cell image data by repeating detection and identification, the detection being for detecting a position of a candidate object, which is a cell object candidate, from a binary image represented by the binary image data, the identification being for identifying partial image data corresponding to the detected position from the cell image data;
a determining unit configured to execute a center determination process for each of the plural pieces of partial image data sequentially, the center determination process including determining, by using the determination data included in the learning data, whether a center of a partial image represented by process target partial image data matches a center of a cell object;
a second image identifying unit, wherein in a case where it is determined in the center determination process for first partial image data among the plural pieces of partial image data that a center of a first partial image represented by the first partial image data does not match a center of a cell object and the first partial image includes a target cell object, the second image identifying unit identifies second partial image data that represents a second partial image including the target cell object from the cell image data, wherein a center of the second partial image matches a center of the target cell object;
a classifying unit configured to classify at least one cell corresponding to at least one cell object among the plurality of cell objects by using a result of the center determination process for each of the plural pieces of partial image data, the classification data included in the learning data and the second partial image data; and
an output unit configured to output a classification result.

2. The image analysis device as in claim 1, further comprising:

a position identifying unit configured to identify a center position of the target cell object included in the first partial image in the case where it is determined in the center determination process for the first partial image data that the center of the first partial image does not match the center of the cell object and the first partial image includes the target cell object; and a changing unit configured to change the binary image data by writing a predetermined mark at a position corresponding to the center position in the binary image represented by the binary image data, wherein the second image identifying unit detects a position of the predetermined mark from a changed binary image represented by the changed binary image data so as to identify the second partial image data corresponding to the position of the predetermined mark from the cell image data.

3. The image analysis device as in claim 2, wherein in a case where it is determined that the center of the first partial image does not match the center of the cell object and the first partial image includes only one target cell object, the position identifying unit identifies one center position, the changing unit changes the binary image data by writing one predetermined mark at one position corresponding to the one center position in the binary image represented by the binary image data, and the second image identifying unit detects a position of the one predetermined mark from the changed binary image represented by the changed binary image data so as to identify the second partial image data corresponding to the position of the one predetermined mark from the cell image data.

4. The image analysis device as in claim 2, wherein in a case where it is determined that the center of the first partial image does not match the center of the cell object and the first partial image includes two or more target cell objects, the position identifying unit identifies two or more center positions, the changing unit changes the binary image data by writing two or more predetermined marks at two or more positions corresponding to the two or more center positions in the binary image represented by the binary image data, and the second image identifying unit detects each of positions of the two or more predetermined marks from the changed binary image represented by the changed binary image data so as to identify two or more second partial image data corresponding to the positions of the two or more predetermined marks from the cell image data.

5. The image analysis device as in claim 4, wherein in a case where the two or more target cell objects include a first cell object having a first center position that is a first distance apart from the center of the first partial image and a second cell object having a second center position that is a second distance apart from the center of the first partial image, the position identifying unit identifies the two or more center positions including the first center position and the second center position, the second distance being longer than the first distance, and the changing unit changes the binary image data by writing the two or more predetermined marks at the two or more positions corresponding to the two or more center positions including the first center position and the second center position in the binary image represented by the binary image data.

6. The image analysis device as in claim 1, wherein the learning data is data for executing image analysis according to a convolutional neural network or image analysis according to a large-scale network including a convolutional neural network as a partial structure thereof.

7. A non-transitory computer-readable medium storing computer-readable instructions for an image analysis device, wherein the image analysis device comprises a memory that stores learning data for image analysis, the learning data including determination data and classification data, the determination data being for determining whether a center of an analysis target image matches a center of a cell object, the classification data being for classifying a cell corresponding to a cell object, and the computer-readable instructions, when executed by a processor of the image analysis device, causing the image analysis device to function as the following units:

an obtaining unit that obtains cell image data representing a cell image including a plurality of cell objects;

a first image identifying unit that identifies sequentially plural pieces of partial image data that represent a plurality of partial images obtained by scanning the cell image data in a matrix pattern with a predetermined interval;

a determining unit that executes a center determination process for each of the plural pieces of partial image data sequentially, the center determination process including determining, by using the determination data included in the learning data, whether a center of a partial image represented by process target partial image data matches a center of a cell object;

a classifying unit that classifies at least one cell corresponding to at least one cell object among the plurality of cell objects by using a result of the center determination process for each of the plural pieces of partial image data and the classification data included in the learning data; and an output unit that outputs a classification result, wherein in a case where it is determined in the center determination process for process target partial image data among the plural pieces of partial image data that a center of a partial image represented by the process target partial image data matches a center of a cell object, the classifying unit classifies a cell corresponding to the cell object, and in a case where it is determined in the center determination process for process target partial image data among the plural pieces of partial image data that a center of a partial image represented by the process target partial image data does not match a center of a cell object, the classifying unit does not execute the classification using the partial image.

8. An image analysis method comprising:

an obtaining step of obtaining cell image data that represents a cell image including a plurality of cell objects;

a first image identifying step of identifying sequentially plural pieces of partial image data that represent a plurality of partial images obtained by scanning the cell image data in a matrix pattern with a predetermined interval;

a determining step of executing a center determination process for each of the plural pieces of partial image data sequentially, the center determination process including determining, by using determination data included in learning data for image analysis, whether a center of a partial image represented by process target partial image data matches a center of a cell object;

a classifying step of classifying at least one cell corresponding to at least one cell object from among the plurality of cell objects by using a result of the center determination process for each of the plural pieces of partial image data and classification data included in the learning data; and an output step of outputting a classification result,
wherein in a case where it is determined in the center determination process for process target partial image data among the plural pieces of partial image data that a center of a partial image represented by the process target partial image data matches a center of a cell object, the classifying step classifies a cell corresponding to the cell object, and in a case where it is determined in the center determination process for process target partial image data among the plural pieces of partial image data that a center of a partial image represented by the process target partial image data does not match a center of a cell object, the classifying step does not execute the classification using the partial image.

9. An image analysis device comprising:

a memory that stores learning data for image analysis, the learning data including determination data and classification data, the determination data being for determining whether a center of an analysis target image matches a center of a cell object, the classification data being for classifying a cell corresponding to a cell object;

an obtaining unit configured to obtain cell image data representing a cell image including a plurality of cell objects;

a first image identifying unit configured to identify sequentially plural pieces of partial image data that represent a plurality of partial images obtained by scanning the cell image data in a matrix pattern with a predetermined interval;

a determining unit configured to execute a center determination process for each of the plural pieces of partial image data sequentially, the center determination process including determining, by using the determination data included in the learning data, whether a center of a partial image represented by process target partial image data matches a center of a cell object, a classifying unit configured to classify at least one cell corresponding to at least one cell object among the plurality of cell objects by using a result of the center determination process for each of the plural pieces of partial image data and the classification data included in the learning data; and an output unit configured to output a classification result,
wherein in a case where it is determined in the center determination process for process target partial image data among the plural pieces of partial image data that a center of a partial image represented by the process target partial image data matches a center of a cell object, the classifying unit classifies a cell corresponding to the cell object, and in a case where it is determined in the center determination process for process target partial image data among the plural pieces of partial image data that a center of a partial image represented by the process target partial image data does not match a center of a cell object, the classifying unit does not execute the classification using the partial image.

10. A non-transitory computer-readable medium storing computer-readable instructions for an image analysis device, wherein:

the image analysis device comprises a memory that stores learning data for image analysis, the learning data including determination data and classification data, the determination data being for determining whether a center of an analysis target image matches a center of a cell object, the classification data being for classifying a cell corresponding to a cell object, and the computer-readable instructions, when executed by a processor of the image analysis device, causing the image analysis device to function as the following units:

an obtaining unit configured to obtain cell image data representing a cell image including a plurality of cell objects;

a generating unit configured to generate binary image data by binarizing the cell image data;

a first image identifying unit that identifies plural pieces of partial image data sequentially from the cell image data by repeating detection and identification, the detection being for detecting a position of a candidate object, which is a cell object candidate, from a binary image represented by the binary image data, the identification being for identifying partial image data corresponding to the detected position from the cell image data;

a determining unit that executes a center determination process for each of the plural pieces of partial image data sequentially, the center determination process including determining, by using the determination data included in the learning data, whether a center of a partial image represented by process target partial image data matches a center of a cell object;

a second image identifying unit, wherein in a case where it is determined in the center determination process for first partial image data among the plural pieces of partial image data that a center of a first partial image represented by the first partial image data does not match a center of a cell object and the first partial image includes a target cell object, the second image identifying unit identifies second partial image data that represents a second partial image including the target cell object from the cell image data, wherein a center of the second partial image matches a center of the target cell object;

a classifying unit that classifies at least one cell corresponding to at least one cell object among the plurality of cell objects by using a result of the center determination process for each of the plural pieces of partial image data, the classification data included in the learning data and the second partial image data; and an output unit that outputs a classification result.

11. An image analysis method comprising:

an obtaining step of obtaining cell image data that represents a cell image including a plurality of cell objects;

a generating step of generating binary image data by binarizing the cell image data;

a first image identifying step of identifying plural pieces of partial image data sequentially from the cell image data by repeating detection and identification, the detection being for detecting a position of a candidate object, which is a cell object candidate, from a binary image represented by the binary image data, the identification being for identifying partial image data corresponding to the detected position from the cell image data;
a determining step of executing a center determination process for each of the plural pieces of partial image data sequentially, the center determination process including determining, by using determination data included in learning data for image analysis, whether a center of a partial image represented by process target partial image data matches a center of a cell object;
a second image identifying step, wherein in a case where it is determined in the center determination process for first partial image data among the plural pieces of partial image data that a center of a first partial image represented by the first partial image data does not match a center of a cell object and the first partial image includes a target cell object, of identifying second partial image data that represents a second partial image including the target cell object from the cell image data, wherein a center of the second partial image matches a center of the target cell object;
a classifying step of classifying at least one cell corresponding to at least one cell object from among the plurality of cell objects by using a result of the center determination process for each of the plural pieces of partial image data and classification data included in the learning data, the classification data included in the learning data and the second partial image data; and
an output step of outputting a classification result.

12. An image analysis device comprising:
a memory that stores learning data for image analysis, the learning data including determination data and classification data, the determination data being for determining whether a center of an analysis target image matches a center of a cell object, the classification data being for classifying a cell corresponding to a cell object;
an obtaining unit configured to obtain cell image data representing a cell image including a plurality of cell objects;
a generating unit configured to generate binary image data by binarizing the cell image data;
a first image identifying unit configured to identify plural pieces of partial image data that represent a plurality of partial images obtained by scanning the cell image data with a predetermined interval;
a determining unit configured to execute a center determination process for each of the plural pieces of partial image data sequentially, the center determination process including determining, by using the determination data included in the learning data, whether a center of a partial image represented by process target partial image data matches a center of a cell object;
a position identifying unit, wherein in a case where it is determined in the center determination process for process target partial image data among the plural pieces of partial image data that a center of a partial image represented by the process target partial image data does not match a center of a cell object and the partial image includes a target cell object, the position identifying unit identifies a center position of the target cell object; and
a changing unit configured to change the binary image data by writing a predetermined mark at a position corresponding to the center position in the binary image represented by the binary image data,
a classifying unit configured to classify at least one cell corresponding to at least one cell object among the plurality of cell objects by using a result of the center determination process for each of the plural pieces of partial image data and the classification data included in the learning data wherein
the classifying unit:
detects a position of the predetermined mark from a changed binary image represented by the changed binary image data;
identifies partial image data corresponding to the detected position from the cell image data; and
classifies a cell corresponding to the target cell object included in a partial image represented by the partial image data by using the partial image data and the classification data; and
an output unit configured to output a classification result.

13. A non-transitory computer-readable medium storing computer-readable instructions, wherein:
the image analysis device comprises a memory that stores learning data for image analysis, the learning data including determination data and classification data, the determination data being for determining whether a center of an analysis target image matches a center of a cell object, the classification data being for classifying a cell corresponding to a cell object, and
the computer-readable instructions, when executed by a processor of the image analysis device, causing the image analysis device to function as the following units:
an obtaining unit that obtains cell image data representing a cell image including a plurality of cell objects;
a generating unit that generates binary image data by binarizing the cell image data;
a first image identifying unit that identifies plural pieces of partial image data that represent a plurality of partial images the cell image data with a predetermined interval;
a determining unit that executes a center determination process for each of the plural pieces of partial image data sequentially, the center determination process including determining, by using the determination data included in the learning data, whether a center of a partial image represented by process target partial image data matches a center of a cell object;
a position identifying unit, wherein in a case where it is determined in the center determination process for process target partial image data among the plural pieces of partial image data that a center of a partial image represented by the process target partial image data does not match a center of a cell object and the partial image includes a target cell object, the position identifying unit identifies a center position of the target cell object; and
a changing unit configured to change the binary image data by writing a predetermined mark at a position corresponding to the center position in the binary image represented by the binary image data;
a classifying unit that classifies at least one cell corresponding to at least one cell object among the plurality of cell objects by using a result of the center determination process for each of the plural pieces of partial image data and the classification data included in the learning data, wherein the classifying unit:
detects a position of the predetermined mark from a changed binary image represented by the changed binary image data;

identifies partial image data corresponding to the detected position from the cell image data; and classifies a cell corresponding to the target cell object included in a partial image represented by the partial image data by using the partial image data and the classification data; and an output unit that outputs a classification result.

14. An image analysis method comprising:

an obtaining step of obtaining cell image data that represents a cell image including a plurality of cell objects;

a generating step of generating binary image data by binarizing the cell image data;

a first image identifying step of identifying plural pieces of partial image data that represent a plurality of partial images obtained by scanning the cell image data with a predetermined interval;

a determining step of executing a center determination process for each of the plural pieces of partial image data sequentially, the center determination process including determining, by using determination data included in learning data for image analysis, whether a center of a partial image represented by process target partial image data matches a center of a cell object;

a position identifying step, wherein in a case where it is determined in the center determination process for process target partial image data among the plural pieces of partial image data that a center of a partial image represented by the process target partial image data does not match a center of a cell object and the partial image includes a target cell object, of identifying a center position of the target cell object; and a changing unit step of changing the binary image data by writing a predetermined mark at a position corresponding to the center position in the binary image represented by the binary image data, a classifying step of classifying at least one cell corresponding to at least one cell object from among the plurality of cell objects by using a result of the center determination process for each of the plural pieces of partial image data and classification data included in the learning data wherein the classifying step comprises:

detecting a position of the predetermined mark from a changed binary image represented by the changed binary image data;

identifying partial image data corresponding to the detected position from the cell image data; and classifies a cell corresponding to the target cell object included in a partial image represented by the partial image data by using the partial image data and the classification data; and an output step of outputting a classification result.

15. The image analysis device as in claim 9, wherein:

the learning data is data for executing image analysis according to a convolutional neural network or image analysis according to a large-scale network including a convolutional neural network as a partial structure thereof.

16. The image analysis device as in claim 12, wherein:

the learning data is data for executing image analysis according to a convolutional neural network or image analysis according to a large-scale network including a convolutional neural network as a partial structure thereof.

* * * * *